(12) United States Patent
Akagane (10) Patent No.: US 9,265,973 B2
(45) Date of Patent: Feb. 23, 2016

(54) ULTRASONIC TREATMENT PROBE PROVIDING SUPERPOSED LATERAL AND LONGITUDINAL VIBRATION

(71) Applicant: Olympus Corporation, Tokyo (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/186,950

(22) Filed: Feb. 21, 2014

(65) Prior Publication Data

US 2014/0221878 A1 Aug. 7, 2014

Related U.S. Application Data

(63) Continuation of application No. PCT/JP2013/065716, filed on Jun. 6, 2013.

(60) Provisional application No. 61/656,163, filed on Jun. 6, 2012.

(51) Int. Cl.
*A61N 7/00* (2006.01)
*A61B 17/32* (2006.01)
*A61B 17/00* (2006.01)

(52) U.S. Cl.
CPC .......... *A61N 7/00* (2013.01); *A61B 17/320068* (2013.01); *A61B 2017/00526* (2013.01); *A61B 2017/320072* (2013.01); *A61B 2017/320076* (2013.01); *Y10T 29/49005* (2015.01)

(58) Field of Classification Search
CPC ............. A61B 17/320092; A61B 2017/00424; A61B 2017/2825; A61B 2017/320072; A61B 17/1606; A61B 17/162; A61B 17/2841; A61B 17/8875; A61B 2017/00477; A61B 17/2812; A61B 17/320068; A61B 17/3201; A61N 7/00
See application file for complete search history.

(56) References Cited

U.S. PATENT DOCUMENTS 6,283,981 B1 9/2001 Beaupre
6,458,143 B1 10/2002 Sugai
(Continued)

FOREIGN PATENT DOCUMENTS

JP U-63-88311 6/1988
JP A-8-224252 9/1996
(Continued)

OTHER PUBLICATIONS

Dec. 18, 2014 International Preliminary Report on Patentability issued in International Application No. PCT/JP2013/065716.
(Continued)

*Primary Examiner* — Amanda Lauritzen Moher
(74) *Attorney, Agent, or Firm* — Oliff PLC (57) ABSTRACT

An ultrasonic probe that transmits an ultrasonic vibration, generated in an ultrasonic vibrator, from a proximal end to a distal end so that the ultrasonic probe performs a longitudinal vibration in a vibrating direction. The ultrasonic probe including a probe body, a distal asymmetric portion, and a proximal side probe component. The distal asymmetric portion is asymmetric about an X-axis so that a center of gravity of the distal asymmetric portion is deviated from the X-axis and a first lateral vibration of the distal asymmetric portion is superposed on the longitudinal vibration of the ultrasonic probe. The proximal side probe component is bent relative to the probe body at a bending position so that a center of gravity of the proximal side component is deviated from the X-axis and a second lateral vibration of the proximal side component is superposed on the longitudinal vibration of the ultrasonic probe.

4 Claims, 9 Drawing Sheets

(56) References Cited

U.S. PATENT DOCUMENTS

| | | |
|---|---|---|
| 2002/0128674 A1 | 9/2002 | Beaupre |
| 2010/0106173 A1 | 4/2010 | Yoshimine |
| 2012/0226165 A1* | 9/2012 | Ogawa .................. 600/462 |

FOREIGN PATENT DOCUMENTS

| | | |
|---|---|---|
| JP | A-2000-70279 | 3/2000 |
| JP | A-2001-104326 | 4/2001 |
| JP | A-2002-253567 | 9/2002 |
| JP | B2-4493893 | 6/2010 |
| WO | WO 2010/047395 A1 | 4/2010 |

OTHER PUBLICATIONS

International Search Report issued in International Application No. PCT/JP2013/065716 mailed Jul. 16, 2013.

* cited by examiner

ULTRASONIC TREATMENT PROBE PROVIDING SUPERPOSED LATERAL AND LONGITUDINAL VIBRATION

CROSS-REFERENCE TO RELATED APPLICATIONS

This is a Continuation Application of PCT Application No. PCT/JP2013/065716, filed Jun. 6, 2013 and based upon and claiming the benefit of priority from prior U.S. Provisional Application No. 61/656,163, filed Jun. 6, 2012, the entire contents of which are incorporated herein by reference.

BACKGROUND OF THE INVENTION

1. Field of the Invention

The present invention relates to an ultrasonic probe which is used in an ultrasonic treatment device, and which is configured to perform longitudinal vibration having a vibration direction parallel to a central axis when ultrasonic vibration is transmitted thereto, and a manufacturing method of the ultrasonic probe.

2. Description of the Related Art

For example, Japanese Patent No. 4493893 has disclosed an ultrasonic treatment device including an ultrasonic probe. The ultrasonic probe of this ultrasonic treatment device is configured to perform longitudinal vibration having a vibration direction (vibration directions) parallel to a central axis when ultrasonic vibration is transmitted thereto. According to Japanese Patent No. 4493893, there are defined an X-axis parallel to longitudinal directions of the ultrasonic probe, a Y-axis which intersects at right angles with the X-axis, and a Z-axis which intersects at right angles with the X-axis and which intersects at right angles with the Y-axis. The ultrasonic probe includes a probe body in which the central axis is coaxial with the X-axis, and a distal asymmetric portion (distal treatment section) provided to a distal direction side of the probe body. The ultrasonic treatment device includes a jaw which can open and close relative to the distal treatment section. The open-and-close directions of the jaw are parallel to the Z-axis. When the ultrasonic probe performs the longitudinal vibration while a treatment target such as a living tissue is grasped between the distal treatment section and the jaw, the grasped treatment target is coagulated and cut, and the treatment target is treated. Here, the probe body is shaped symmetrically with an X-Z plane, which is defined by the X-axis and the Z-axis, being a center. The distal treatment section is curved relative to the probe body in directions parallel to the Y-axis, for example, to ensure visibility for a surgeon during the treatment of the treatment target. Therefore, the distal treatment section is shaped asymmetrically with the X-Z plane, which is defined by the X-axis and the Z-axis, being the center.

BRIEF SUMMARY OF THE INVENTION

According to one aspect of the invention, a manufacturing method of an ultrasonic probe which extends from a proximal end to a distal end along a central axis and which is configured to perform a longitudinal vibration having a vibration direction parallel to the central axis when an ultrasonic vibration is transmitted thereto, an X-axis parallel to longitudinal directions, a Y-axis which intersects at right angles with the X-axis, and a Z-axis which intersects at right angles with the X-axis and which intersects at right angles with the Y-axis being defined in the ultrasonic probe, a distal asymmetric portion, which is shaped asymmetrically with an X-Z plane being a center, being provided in a distal-direction side part of the ultrasonic probe, the X-Z plane being defined by the X-axis and the Z-axis, the manufacturing method including: analyzing a first lateral vibration which is superposed on the longitudinal vibration because of an asymmetric shape of the distal asymmetric portion when the ultrasonic probe is longitudinally vibrated, the first lateral vibration having a vibration direction which is parallel to an X-Y plane defined by the X-axis and the Y-axis and which is perpendicular to the central axis; specifying a bending position to bend a proximal-direction side part of the ultrasonic probe so that the proximal-direction side part is parallel to the X-Y plane and tilted relative to the X-axis, a second lateral vibration, which has the same wavelength and vibration direction as the first lateral vibration and which is in anti-phase with respect to the first lateral vibration, being superposed on the longitudinal vibration and the first lateral vibration in the ultrasonic probe when the ultrasonic probe is longitudinally vibrated while the ultrasonic probe is bent at the bending position; and forming a proximal side probe component which bends the ultrasonic probe at the specified bending position and in which the central axis is bent relative to the X-axis.

According to one another aspect of the invention, an ultrasonic probe which extends from a proximal end to a distal end along a central axis and which is configured to perform a longitudinal vibration having a vibration direction parallel to the central axis when an ultrasonic vibration is transmitted thereto, the ultrasonic probe including: a probe body in which the central axis is coaxial with an X-axis, and which is shaped symmetrically with an X-Z plane defined by the X-axis and a Z-axis being a center, when the X-axis parallel to longitudinal directions, a Y-axis which intersects at right angles with the X-axis, and the Z-axis which intersects at right angles with the X-axis and which intersects at right angles with the Y-axis are defined; a distal asymmetric portion which is provided to a distal-direction side of the probe body, and which is shaped asymmetrically with the X-Z plane being the center, a first lateral vibration, having a vibration direction which is parallel to an X-Y plane defined by the X-axis and the Y-axis and which is perpendicular to the central axis, being superposed on the longitudinal vibration in the ultrasonic probe when the ultrasonic probe is longitudinally vibrated because of an asymmetric shape of the distal asymmetric portion; and a proximal side probe component which is provided to a proximal-direction side of the probe body, and which is bent relative to the probe body at a bending position so that the proximal side probe component is parallel to the X-Y plane and tilted relative to the X-axis, a second lateral vibration, which has the same wavelength and vibration direction as the first lateral vibration and which is in anti-phase with respect to the first lateral vibration, being superposed on the longitudinal vibration and the first lateral vibration in the ultrasonic probe when the ultrasonic probe is longitudinally vibrated because the proximal side probe component is bent relative to the probe body at the bending position.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

Figure 1:
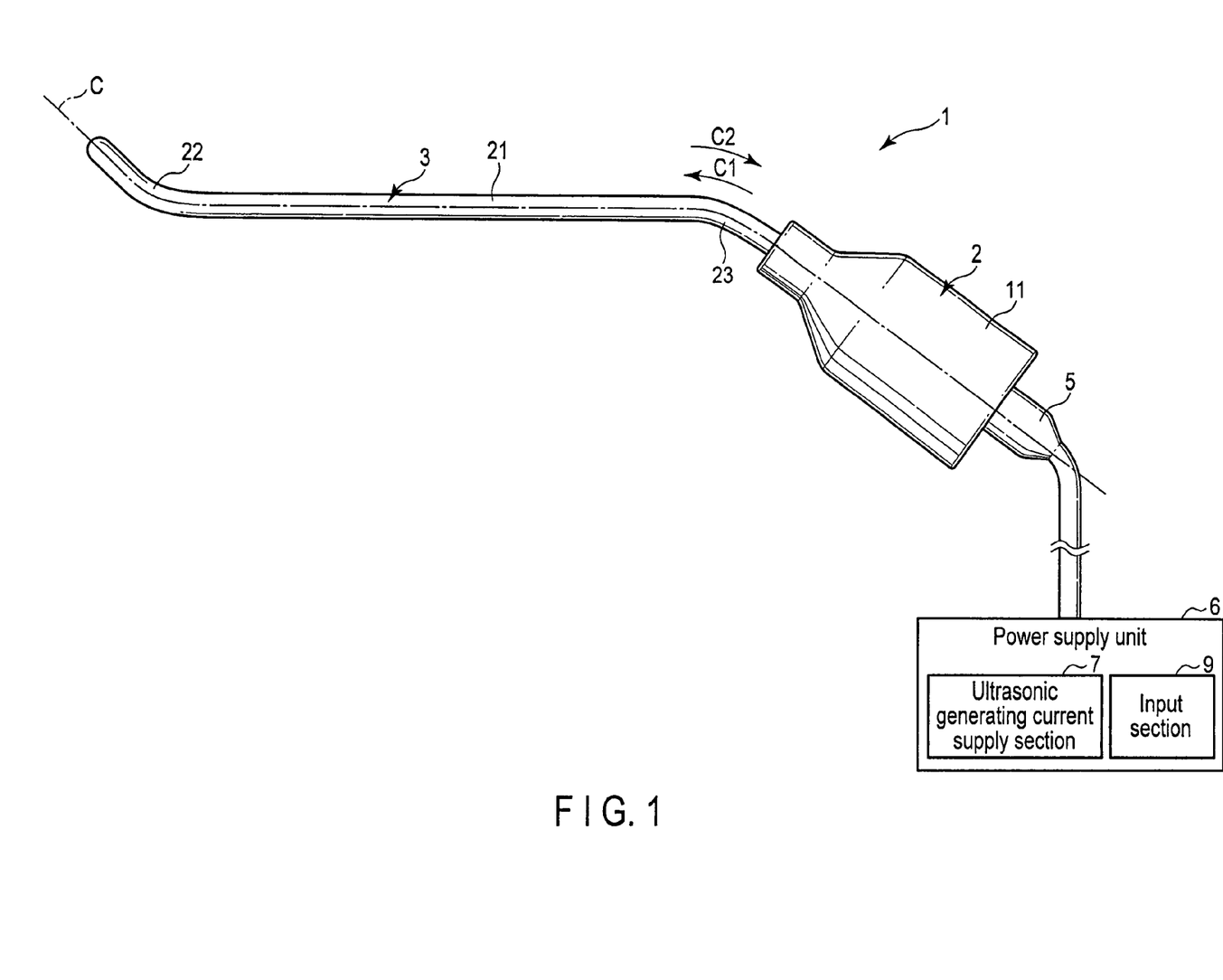
FIG. 1 is a schematic diagram showing an ultrasonic treatment device according to a first embodiment of the present invention.

A first embodiment of the present invention is described with reference to FIG. 1 to FIG. 10. FIG. 1 is a diagram showing an ultrasonic treatment device 1 according to the present embodiment. As shown in FIG. 1, the ultrasonic treatment apparatus 1 has a central axis C. Here, one of two directions parallel to the central axis C is a distal direction (direction of an arrow C1 in FIG. 1), and the direction opposite to the distal direction is a proximal direction (direction of an arrow C2 in FIG. 1). The ultrasonic treatment device 1 includes a vibration generating unit 2, and an ultrasonic probe 3 extending from a proximal end to a distal end along the central axis C. In FIG. 1, FIG. 3, FIG. 4, and FIG. 10, the curving of the ultrasonic probe 3 is exaggerated for ease of understanding. Therefore, the degree of this curving is different from that of the actual curving of the ultrasonic probe 3.

The vibration generating unit 2 includes a vibrator case 11. One end of a cable 5 is connected to the proximal end of the vibrator case 11. The other end of the cable 5 is connected to a power supply unit 6. The power supply unit 6 includes an ultrasonic generating current supply section 7, and an input section 9.

Figure 2:
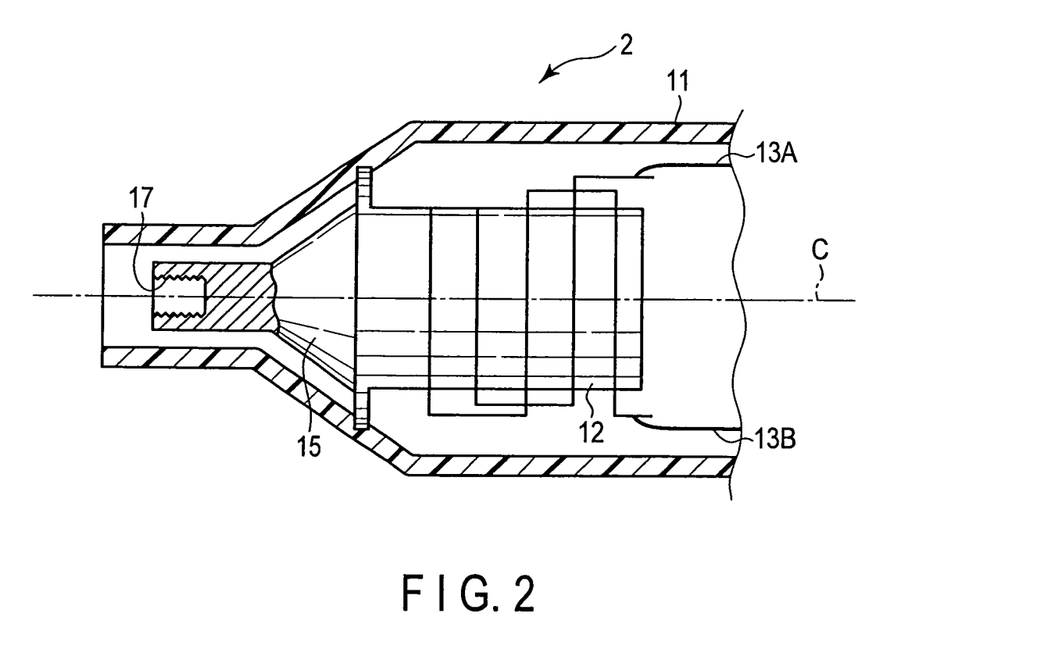
FIG. 2 is a sectional view schematically showing the configuration of a vibration generating unit according to the first embodiment.

FIG. 2 is a diagram showing the configuration of the vibration generating unit 2. As shown in FIG. 2, an ultrasonic vibrator 12, which is a vibration generator including a piezoelectric element configured to convert a current to an ultrasonic vibration, is provided inside the transducer case 11. One end of each of electric wiring lines 13A and 13B is connected to the ultrasonic transducer 12. Each of the electric wiring lines 13A and 13B has the other end connected to the ultrasonic generating current supply section 7 of the power supply unit 6 through an inside of the cable 5. The ultrasonic vibration is generated in the ultrasonic vibrator 12 by the supply of a current to the ultrasonic oscillator 12 from the ultrasonic generating current supply section 7 via the electric wiring lines 13A and 13B. A horn 15 which is configured to increase the amplitude of the ultrasonic vibration is coupled to the distal-direction side of the ultrasonic vibrator 12. The horn 15 is attached to the oscillator case 11. An internal thread portion 17 is formed in a distal portion of the horn 15.

Figure 3:
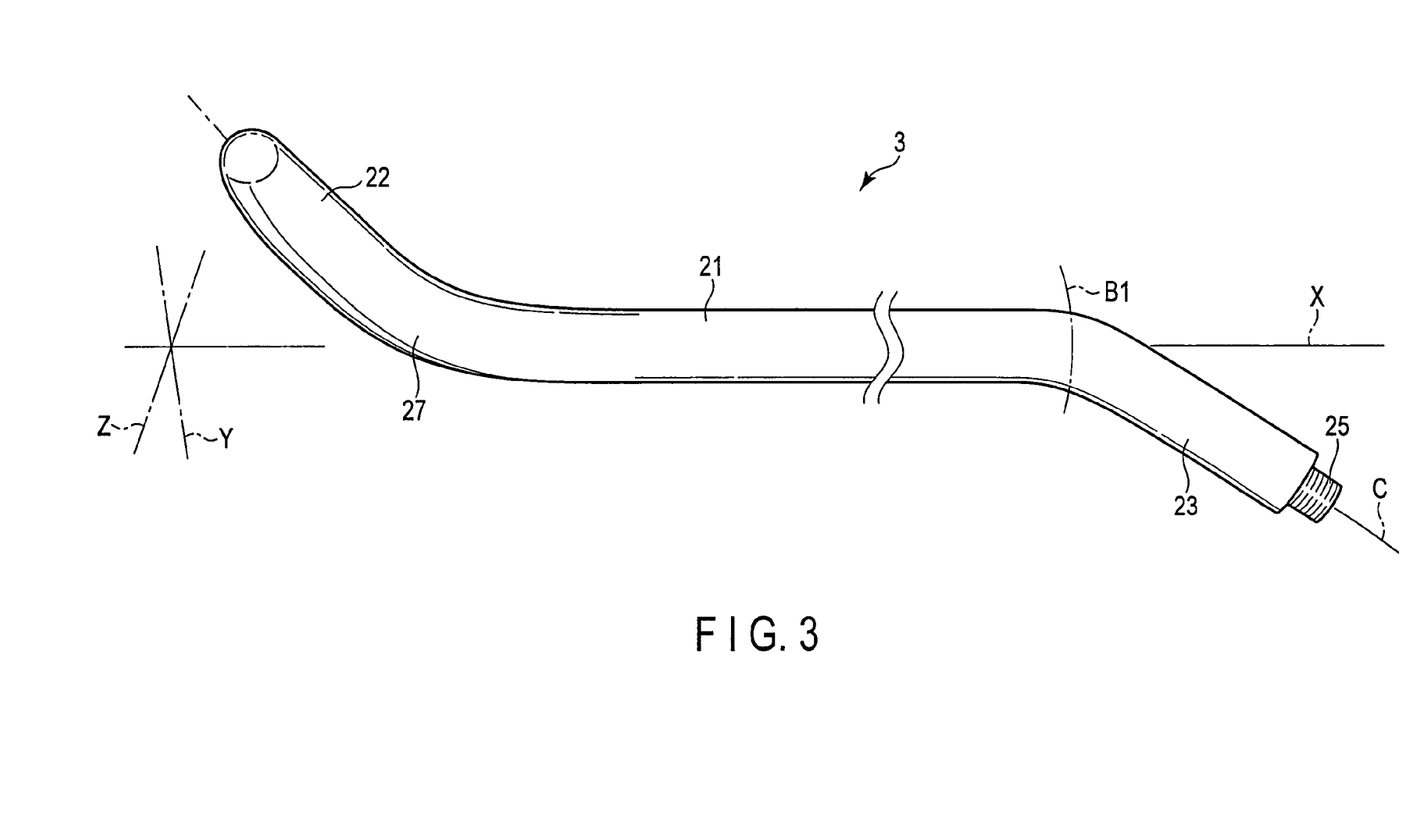
FIG. 3 is a perspective view schematically showing the configuration of an ultrasonic probe according to the first embodiment.
Figure 4:
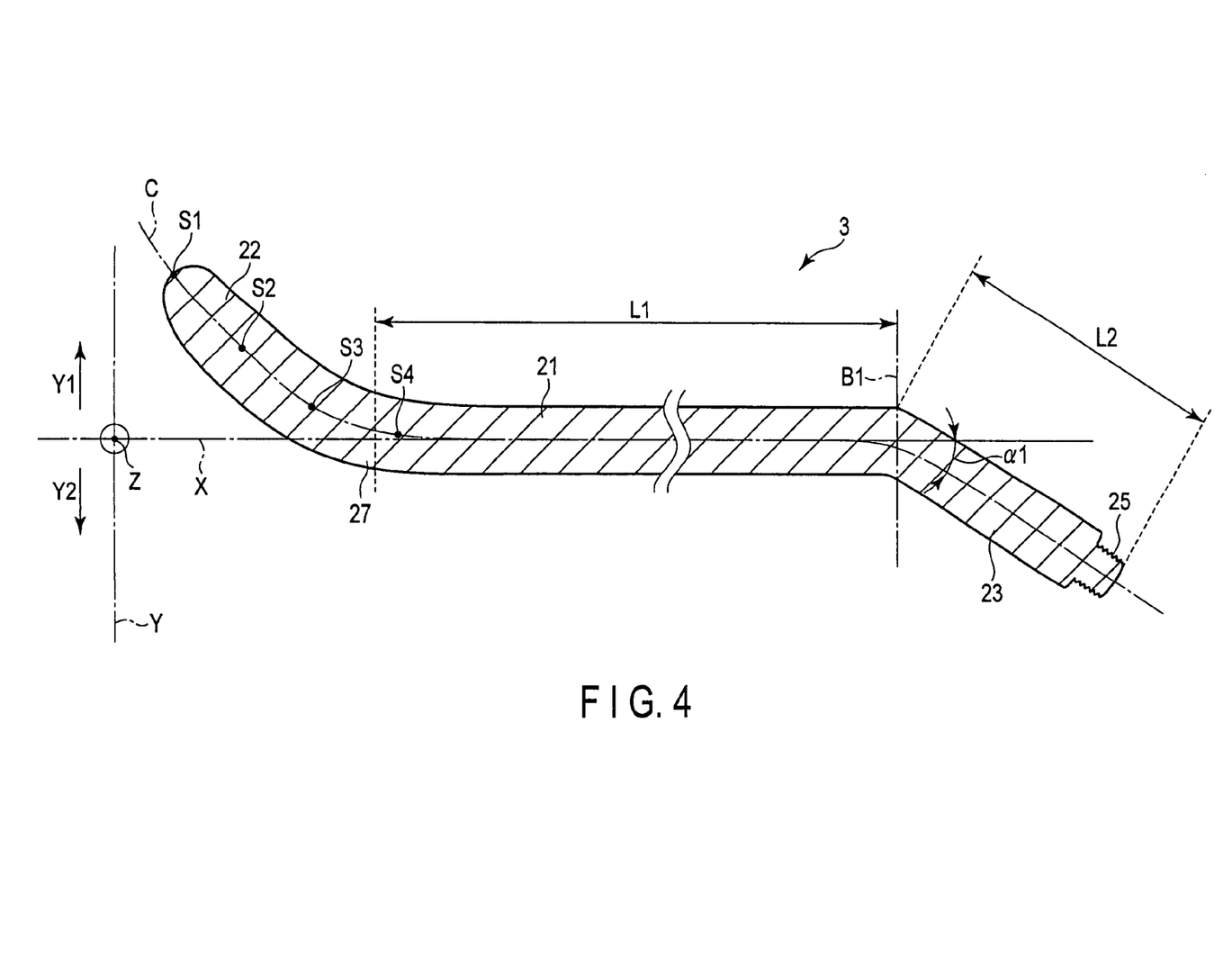
FIG. 4 is a sectional view schematically showing the configuration of the ultrasonic probe according to the first embodiment.

FIG. 3 and FIG. 4 are diagrams showing the ultrasonic probe 3. As shown in FIG. 3 and FIG. 4, the ultrasonic probe 3 includes a probe body 21, a distal asymmetric portion 22 provided to the distal-direction side of the probe body 21, and a proximal side probe component 23 provided to the proximal-direction side of the probe body 21. A treatment region (treatment section) configured to treat a living tissue is formed in the distal asymmetric portion 22.

An external thread portion 25 is formed in an outer peripheral portion of the proximal side probe component 23. The external thread portion 25 is threaded into the internal thread portion 17 of the horn 15, and the ultrasonic probe 3 is thereby attached to the vibration generating unit 2. When the ultrasonic probe 3 is attached to the vibration generating unit 2, the ultrasonic vibration generated in the ultrasonic vibrator 12 is transmitted to the ultrasonic probe 3. When the ultrasonic vibration is transmitted to the ultrasonic probe 3, the ultrasonic probe 3 can perform a longitudinal vibration having a vibration direction (vibration directions) and a transmission direction parallel to the central axis C.

The probe body 21 extends along longitudinal directions. In the probe body 21, the central axis C is coaxial with an X-axis parallel to the longitudinal directions. Here, a Y-axis which intersects at right angles with the X-axis, and a Z-axis which intersects at right angles with the X-axis and which intersects at right angles with the Y-axis are defined. One of directions parallel to the Y-axis is a first Y-axis direction (direction of an arrow Y1 in FIG. 4), and the direction opposite to the first Y-axis direction is a second Y-axis direction (direction of an arrow Y2 in FIG. 4). FIG. 4 shows a sectional view of the ultrasonic probe 3 in an X-Y plane defined by the X-axis and the Y-axis. The probe body 21 is shaped symmetrically with an X-Z plane, which is defined by the X-axis and the Z-axis, being a center.

The distal asymmetric portion 22 includes a curved part 27 which is curved relative to the X-axis toward the first Y-axis direction. The provision of the curved part 27 ensures visibility for a surgeon in the treatment of a treatment target with the distal asymmetric portion 22. Since the curved part 27 is provided, the distal asymmetric portion 22 is shaped asymmetrically with the X-Z plane being center. Therefore, the center of gravity of the distal asymmetric portion 22 is located away from the X-axis toward the first Y-axis direction which is one of the directions parallel to the Y-axis.

The proximal side probe component 23 is bent relative to the probe body 21 at a bending position B1. The proximal side probe component 23 extends parallel to the X-Y plane and is tilted relative to the X-axis. At the bending position B1, the proximal side probe component 23 is bent at a bending angle $\alpha 1$ with respect to the probe body 21 (X-axis). The proximal side probe component 23 is slanted relative to the X-axis toward the second Y-axis direction which is the other of the directions parallel to the Y-axis. Therefore, the center of gravity of the proximal side probe component 23 is located away from the X-axis toward the second Y-axis direction.

The proximal side probe component 23 extends to the bending position B1 from a proximal end of the ultrasonic probe 3 along the central axis C. A first dimension L1 of the probe body 21 along the central axis C (X-axis) is larger than a second dimension L2 of the proximal side probe component 23 along the central axis C. Therefore, the bending position B1 is located in a proximal-direction side part of the ultrasonic probe 3.

Now, the functions of the ultrasonic treatment device 1 and the ultrasonic probe 3 are described. When a treatment target such as a living tissue is treated with the distal asymmetric portion 22 of the ultrasonic probe 3, a current is supplied to the ultrasonic vibrator 12 from the ultrasonic generating current supply section 7 via the electric wiring lines 13A and 13B by the operation in the input section 9. As a result, the ultrasonic vibration is generated in the ultrasonic vibrator 12, and the ultrasonic vibration is transmitted to the ultrasonic probe 3 through the horn 15. When the ultrasonic vibration is transmitted to the ultrasonic probe 3, the ultrasonic probe 3 performs the longitudinal vibration having a vibration direction and a transmission direction parallel to the central axis C. While the ultrasonic probe 3 is performing the longitudinal vibration, the distal asymmetric portion 22 treats the treatment target. For example, when the ultrasonic probe 3 performs the longitudinal vibration while the distal asymmetric portion 22 is in contact with the treatment target, the treatment target is coagulated and cut by the distal asymmetric portion 22. In this case, the curved part 27 is provided in the distal asymmetric portion 22, so that the visibility for the surgeon is ensured. Although not shown, a jaw which can open and close relative to the distal asymmetric portion 22 may be provided to grasp and thus treat the tissue of the treatment target.

Here, since the curved part 27 is provided, the distal asymmetric portion 22 is shaped asymmetrically with respect to the X-Z plane. That is, the center of gravity of the distal asymmetric portion 22 is located away from the X-axis toward the first Y-axis direction which is one of the directions parallel to the Y-axis. Because of the asymmetric shape of the distal asymmetric portion 22, a first lateral vibration is superposed on the longitudinal vibration in the ultrasonic probe 3 while the ultrasonic probe 3 is performing the longitudinal vibration. The vibration direction (vibration directions) of the first lateral vibration is parallel to the X-Y plane and perpendicular to the central axis C.

Figure 5:
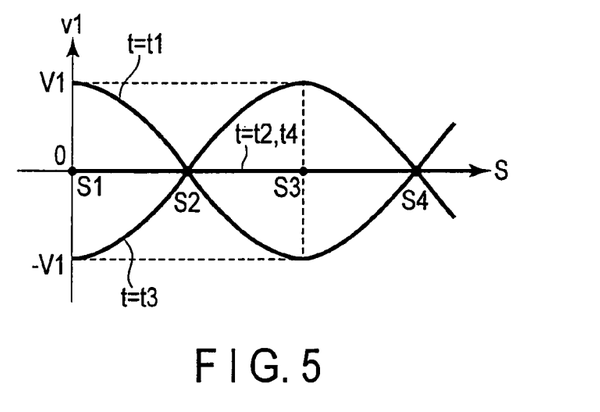
FIG. 5 is a schematic diagram showing the change of a first lateral vibration relative to the change of the position along the central axis of the ultrasonic probe according to the first embodiment.
Figure 6:
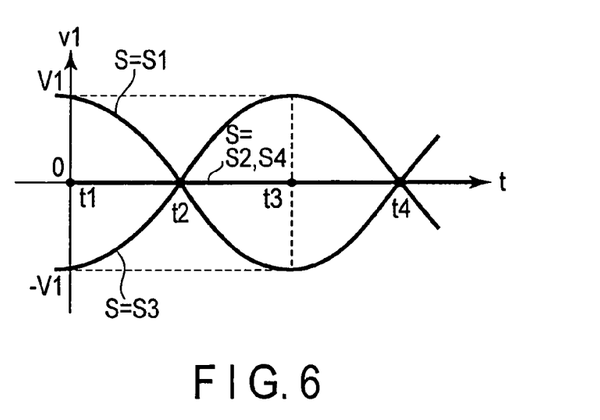
FIG. 6 is a schematic diagram showing the change of a first lateral vibration relative to the change of time at each of the positions along the central axis of the ultrasonic probe according to the first embodiment.

FIG. 5 is a graph showing the change of the first lateral vibration (v1) relative to the change of the position (S) along the central axis C. FIG. 6 is a graph showing the change of the first lateral vibration (v1) relative to the change of time (t) at each of positions S1 to S4. Here, the positions S1 to S4 correspond to the positions S1 to S4 in FIG. 4. FIG. 5 shows the change of the first lateral vibration (v1) relative to the change of the position (S) along the central axis C when the time (t) is t1, t2, t3, and t4.

As shown in FIG. 5 and FIG. 6, the positions S1 and S3 are anti-node positions of the first lateral vibration, and the positions S2 and S4 are node positions of the first lateral vibration. The change of the first lateral vibration relative to the change of time at the position S1 is in anti-phase with respect to the change of the first lateral vibration relative to the change of time at the position S3. The change of the first lateral vibration relative to the change of time at the position S2 is in anti-phase with respect to the change of the first lateral vibration relative to the change of time at the position S4. The first lateral vibration has a first amplitude V1.

The proximal side probe component 23 is bent relative to the probe body 21 at the bending position B1 so that the proximal side probe component 23 is parallel to the X-Y plane and inclined relative to the X-axis. That is, the center of gravity of the proximal side probe component 23 is located away from the X-axis toward the second Y-axis direction which is the other of the directions parallel to the Y-axis. Because the proximal side probe component 23 is bent relative to the probe body 21 at the bending position B1, a second lateral vibration is superposed on the longitudinal vibration and the first lateral vibration in the ultrasonic probe 3 while the ultrasonic probe 3 is performing the longitudinal vibration. The vibration direction (vibration directions) of the second lateral vibration is parallel to the X-Y plane and perpendicular to the central axis C. That is, the vibration direction of the second lateral vibration is the same as the vibration direction of the first lateral vibration.

Figure 7:
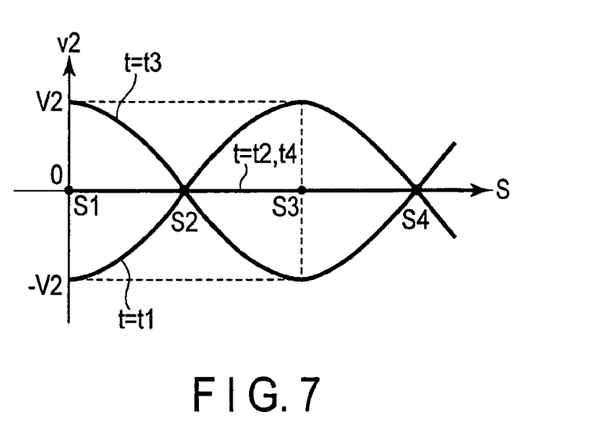
FIG. 7 is a schematic diagram showing the change of a second lateral vibration relative to the change of the position along the central axis of the ultrasonic probe according to the first embodiment.
Figure 8:
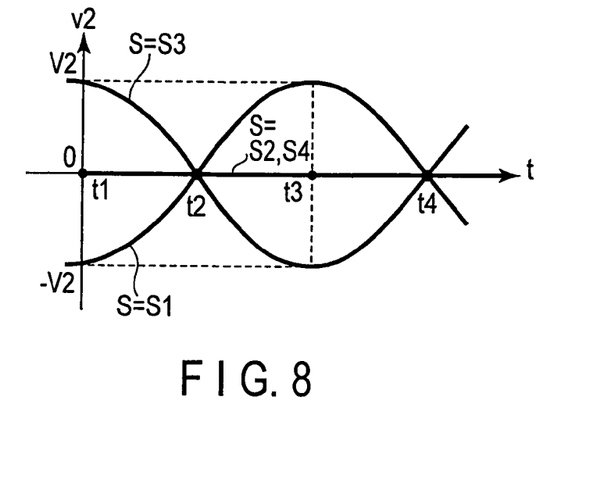
FIG. 8 is a schematic diagram showing the change of a second lateral vibration relative to the change of time at each of the positions along the central axis of the ultrasonic probe according to the first embodiment.

FIG. 7 is a graph showing the change of the second lateral vibration (v2) relative to the change of the position (S) along the central axis C. FIG. 8 is a graph showing the change of the second lateral vibration (v2) relative to the change of time (t) at each of the positions S1 to S4. Here, the positions S1 to S4 correspond to the positions S1 to S4 in FIG. 4. FIG. 7 shows the change of the second lateral vibration (v2) relative to the change of the position (S) along the central axis C when the time (t) is t1, t2, t3, and t4.

As shown in FIG. 7 and FIG. 8, the positions S1 and S3 are anti-node positions of the second lateral vibration, and the positions S2 and S4 are node positions of the second lateral vibration. The change of the second lateral vibration relative to the change of time at the position S1 is in anti-phase with respect to the change of the second lateral vibration relative to the change of time at the position S3. The change of the second lateral vibration relative to the change of time at the position S2 is in anti-phase with respect to the change of the second lateral vibration relative to the change of time at the position S4.

Compared to the first lateral vibration (FIG. 5 and FIG. 6), the change of the second lateral vibration relative to the change of time at the position S1 is in anti-phase with respect to the change of the first lateral vibration relative to the change of time at the position S1. The same applies to the positions S2 to S4. That is, the wavelength of the second lateral vibration is the same as the wavelength of the first lateral vibration, and the second lateral vibration is in anti-phase with respect to the first lateral vibration.

The second lateral vibration has a second amplitude V2. The degree of the second amplitude V2 depends on the bending angle $\alpha 1$ of the proximal side probe component 23 with respect to the probe body 21 at the bending position B1. The bending angle $\alpha 1$ is set so that the second amplitude V2 is the same as the first amplitude V1.

As described above, while the ultrasonic probe 3 is performing the longitudinal vibration, the second lateral vibration, which has the same wavelength and vibration direction as the first lateral vibration and which is in anti-phase with respect to the first lateral vibration, is superposed on the longitudinal vibration in addition to the first lateral vibration. Therefore, the first lateral vibration and the second lateral vibration interfere with each other, so that the influence of the first lateral vibration and the second lateral vibration on the longitudinal vibration of the ultrasonic probe 3 is inhibited. That is, the influence of the first lateral vibration and the second lateral vibration is inhibited in at least the distal asymmetric portion 22. When the influence of the first lateral vibration and the second lateral vibration is thus inhibited, the ultrasonic probe 3 vibrates in a vibration mode suitable for the treatment. That is, the ultrasonic probe 3 suitably performs the longitudinal vibration, and the longitudinal vibration for use in the treatment is suitably transmitted to the distal asymmetric portion 22. Because the influence of the first lateral vibration and the second lateral vibration is inhibited, the generation of cavitation in the outer circumferential portion of the ultrasonic probe 3 is efficiently prevented, and the deterioration of treatment performance is prevented.

The second amplitude V2 of the second lateral vibration is the same as the first amplitude V1 of the first lateral vibration. Therefore, the first lateral vibration and the second lateral vibration interfere with each other, so that the influence of the first lateral vibration and the second lateral vibration on the longitudinal vibration of the ultrasonic probe 3 is eliminated. Because the influence of the first lateral vibration and the second lateral vibration is eliminated, the ultrasonic probe 3 more suitably performs the longitudinal vibration, and the longitudinal vibration for use in the treatment is more suitably transmitted to the distal asymmetric portion 22.

The center of gravity of the distal asymmetric portion 22 is located away from the X-axis toward the first Y-axis direction which is one of the directions parallel to the Y-axis. The proximal side probe component 23 is tilted relative to the X-axis toward the second Y-axis direction which is the direction opposite to the first Y-axis direction. Therefore, the center of gravity of the proximal side probe component 23 is located away from the X-axis toward the second Y-axis direction. The center of gravity of the distal asymmetric portion 22 is located away from the X-axis toward the first Y-axis direction, and the center of gravity of the proximal side probe component 23 is located away from the X-axis toward the second Y-axis direction, so that the center of gravity of the whole ultrasonic probe 3 is located in the vicinity of the X-axis. Because the center of gravity of the ultrasonic probe 3 is located in the vicinity of the X-axis, the weight balance of the ultrasonic probe 3 is ensured, and the surgeon can easily move the ultrasonic probe 3, for example.

The first dimension L1 of the probe body 21 along the central axis C is larger than the second dimension L2 of the proximal side probe component 23 along the central axis C. Therefore, the bending position B1 is located in the proximal-direction side part of the ultrasonic probe 3. Because the first dimension L1 along the central axis C of the probe body 21 in which the central axis C is coaxial with the X-axis is larger, the weight balance of the ultrasonic probe 3 is ensured, and the surgeon can easily move the ultrasonic probe 3, for example.

Figure 9:
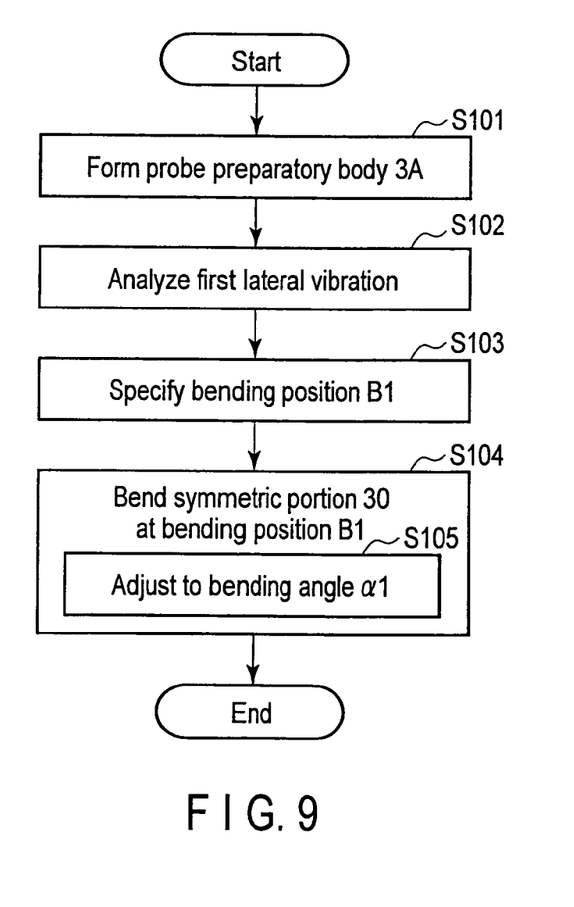
FIG. 9 is a flowchart showing a manufacturing method of the ultrasonic probe according to the first embodiment.

Now, a manufacturing method of the ultrasonic probe 3 is described. FIG. 9 is a flowchart showing the manufacturing method of the ultrasonic probe 3. As shown in FIG. 9, a probe preparatory body 3A is first formed (step S101), when the ultrasonic probe 3 is manufactured.

Figure 10:
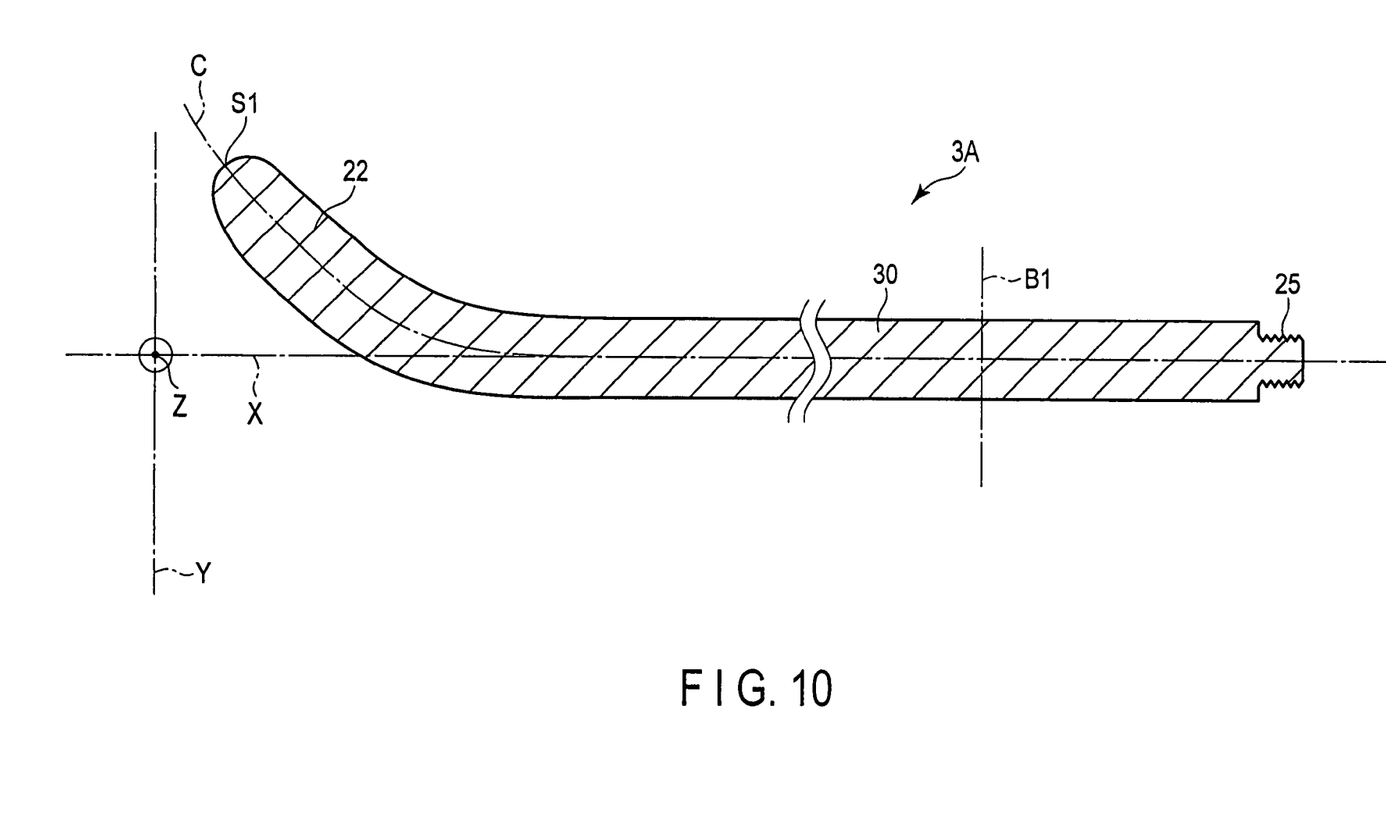
FIG. 10 is a sectional view schematically showing the configuration of a probe preparatory body according to the first embodiment.

FIG. 10 is a sectional view of the probe preparatory body 3A in the X-Y plane. In the probe preparatory body 3A, the X-axis, the Y-axis, and the Z-axis are defined as in the ultrasonic probe 3. As shown in FIG. 10, the probe preparatory body 3A includes a symmetric portion 30 in which the central axis C is coaxial with the X-axis, and a distal asymmetric portion 22 provided to the distal-direction side of the symmetric portion 30. The distal asymmetric portion 22 is formed into a shape similar to the shape of the distal asymmetric portion 22 of the ultrasonic probe 3, and serves as the distal asymmetric portion 22 of the ultrasonic probe 3. Therefore, the center of gravity of the distal asymmetric portion 22 is located away from the X-axis toward the first Y-axis direction which is one of the directions parallel to the Y-axis. The symmetric portion 30 is shaped symmetrically with the X-Z plane being the center. The symmetric portion 30 serves as the probe body 21 and the proximal side probe component 23 of the ultrasonic probe 3. The symmetric portion 30 extends from a proximal end of the probe preparatory body 3A along the X-axis (central axis C).

After the probe preparatory body 3A is formed, the probe preparatory body 3A is longitudinally vibrated by the transmission of the ultrasonic vibration to the probe preparatory body 3A. As shown in FIG. 9, while the probe preparatory body 3A is being longitudinally vibrated, the first lateral vibration superposed on the longitudinal vibration is analyzed (step S102). Because of the shape of the distal asymmetric portion 22 which is asymmetric with the X-Z plane being the center, the first lateral vibration is superposed on the longitudinal vibration. Vibration characteristics of the first lateral vibration such as the vibration direction, wavelength, anti-node position, node position, and phase are as have been described with reference to FIG. 5 and FIG. 6.

The bending position B1 to bend the symmetric portion 30 is then specified (step S103). At the bending position B1, the symmetric portion 30 is bent so that the proximal side probe component 23 located to the proximal-direction side of the bending position B1 is parallel to the X-Y plane and tilted relative to the X-axis. When the probe preparatory body 3A is longitudinally vibrated while the symmetric portion 30 is bent at the bending position B1, the second lateral vibration is superposed on the longitudinal vibration and the first lateral vibration. The second lateral vibration has the same wavelength and vibration direction as the first lateral vibration, and is in anti-phase with the first lateral vibration. Vibration characteristics of the second lateral vibration such as the vibration direction, wavelength, anti-node position, node position, and phase are as have been described with reference to FIG. 7 and FIG. 8.

To specify the bending position B1, for example, the symmetric portion 30 is bent at a given temporary position, and vibration characteristics when the probe preparatory body 3A bent at the temporary position is longitudinally vibrated are analyzed by a simulation. The temporary position to bend the symmetric portion 30 is changed along the central axis C (X-axis) in accordance with, for example, the analyzed vibration characteristics of the first lateral vibration, and the simulation of the vibration characteristics in which the probe preparatory body 3A is longitudinally vibrated is repeated.

In the present embodiment, the bending position B1 is specified so that the proximal side probe component 23 located to the proximal-direction side of the bending position B1 is tilted relative to the X-axis toward the second Y-axis direction which is the direction opposite to the first Y-axis direction. The bending position B1 is also specified so that the first dimension L1 of the probe body 21 along the central axis C (X-axis) is larger than the second dimension L2 of the proximal side probe component 23 along the central axis C.

The symmetric portion 30 is then bent at the specified bending position B1 (step S104). As a result, the probe body 21 and the proximal side probe component 23 of the ultrasonic probe 3 are formed. In this case, the angle between the probe body 21 (X-axis) and the proximal side probe component 23 at the bending position B1 is adjusted to the bending angle α1 (step S105). As a result, the second amplitude V2 of the second lateral vibration is adjusted to be the same as the first amplitude V1 of the first lateral vibration. In this way, the ultrasonic probe 3 is manufactured.

Accordingly, the ultrasonic probe 3 having the configuration described above and the manufacturing method of the ultrasonic probe 3 have the following advantageous effects. That is, the proximal side probe component 23 is bent relative to the probe body 21 at the bending position B1 so that the proximal side probe component 23 is parallel to the X-Y plane and slanted relative to the X-axis. Thus, while the ultrasonic probe 3 is performing the longitudinal vibration, the second lateral vibration, which has the same wavelength and vibration direction as the first lateral vibration and which is in anti-phase with the first lateral vibration, is superposed on the longitudinal vibration in addition to the first lateral vibration. Therefore, the first lateral vibration and the second lateral vibration interfere with each other, so that the influence of the first lateral vibration and the second lateral vibration on the longitudinal vibration of the ultrasonic probe 3 is inhibited. Because the influence of the first lateral vibration and the second lateral vibration is inhibited, the ultrasonic probe 3 vibrates in a vibration mode suitable for the treatment. That is, the ultrasonic probe 3 suitably performs the longitudinal vibration, and the longitudinal vibration for use in the treatment can be suitably transmitted to the distal asymmetric portion 22. Because the influence of the first lateral vibration and the second lateral vibration is inhibited, the generation of cavitation in the outer peripheral portion of the ultrasonic probe 3 is efficiently prevented, and the deterioration of treatment performance is prevented.

In the ultrasonic probe 3, the angle between the probe body 21 and the proximal side probe component 23 at the bending position B1 is adjusted to the bending angle α1. As a result, the second amplitude V2 of the second lateral vibration is adjusted to be the same as the first amplitude V1 of the first lateral vibration. Therefore, the first lateral vibration and the second lateral vibration interfere with each other, so that the influence of the first lateral vibration and the second lateral vibration on the longitudinal vibration of the ultrasonic probe 3 is eliminated. Because the influence of the first lateral vibration and the second lateral vibration is eliminated, the ultrasonic probe 3 more suitably performs the longitudinal vibration, and the longitudinal vibration for use in the treatment can be more suitably transmitted to the distal asymmetric portion 22.

(Modifications)

Figure 11:
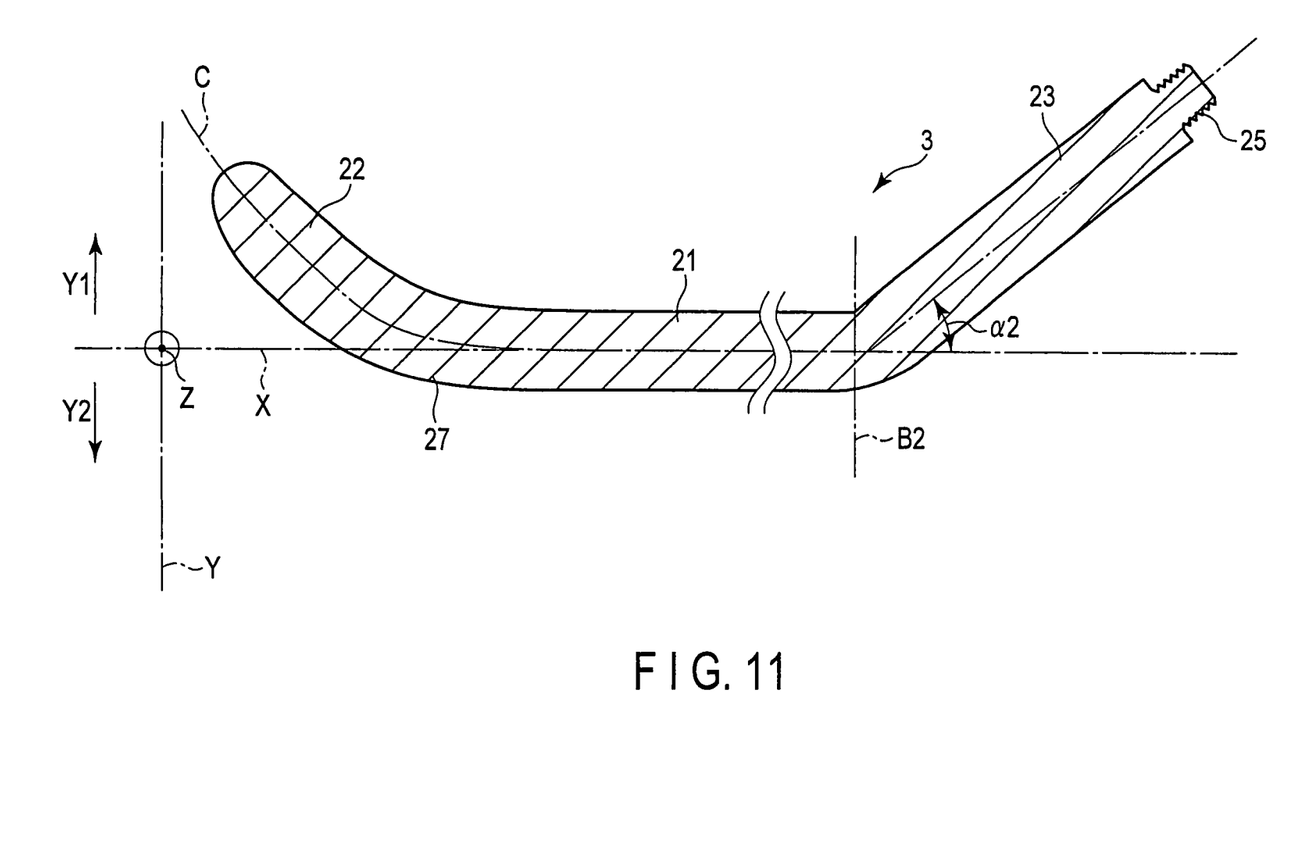
FIG. 11 is a sectional view schematically showing the configuration of an ultrasonic probe according to a first modification.

Although the proximal side probe component 23 is bent relative to the probe body 21 at the bending position B1 so that the proximal side probe component 23 is tilted relative to the X-axis toward the second Y-axis direction in the first embodiment, this is not a restriction. For example, as in a first modification shown in FIG. 11, the proximal side probe component 23 may be bent relative to the probe body 21 at a bending position B2. In FIG. 11, the curving of the ultrasonic probe 3 is exaggerated for ease of understanding. Therefore, the degree of this curving is different from that of the actual curving of the ultrasonic probe 3.

The bending position B2 is a position different from the bending position B1 along the central axis C. In the present modification, the proximal side probe component 23 is bent relative to the probe body 21 at the bending position B2 so that the proximal side probe component 23 is parallel to the X-Y plane and tilted relative to the X-axis, as in the first embodiment.

However, in the present modification, the proximal side probe component 23 is bent relative to the probe body 21 at the bending position B2 so that the proximal side probe component 23 is slanted relative to the X-axis toward the first Y-axis direction. Therefore, in the present modification, the center of gravity of the distal asymmetric portion 22 is located away from the X-axis toward the first Y-axis direction, and the center of gravity of the proximal side probe component 23 is located away from the X-axis toward the first Y-axis direction. Thus, the center of gravity of the whole ultrasonic probe 3 is located away from the X-axis toward the first Y-axis direction, compared to the first embodiment. In consequence, the weight balance of the ultrasonic probe 3 deteriorates compared to the first embodiment.

In the present modification, because the proximal side probe component 23 is bent relative to the probe body 21 at the bending position B2, the second lateral vibration is superposed on the longitudinal vibration and the first lateral vibration in the ultrasonic probe 3 while the ultrasonic probe 3 is performing the longitudinal vibration. As has been described above in the first embodiment, the second lateral vibration has the same wavelength and vibration direction as the first lateral vibration, and is in anti-phase with respect to the first lateral vibration. As described above, the bending position (B1, B2) to superpose the second lateral vibration on the longitudinal vibration and the first lateral vibration is not limited to one bending position.

At the bending position B2, the proximal side probe component 23 is bent at a bending angle α2 with respect to the probe body 21 (X-axis). That is, the angle between the probe body 21 and the proximal side probe component 23 at the bending position B2 is adjusted to the bending angle α2. As a result, the second amplitude V2 of the second lateral vibration is adjusted to be the same as the first amplitude V1 of the first lateral vibration.

According to the first modification described above, the proximal side probe component 23 has only to be bent relative to the probe body 21 at the bending position (B1; B2) so that the proximal side probe component 23 is parallel to the X-Y plane and tilted relative to the X-axis. The proximal side probe component 23 is bent relative to the probe body 21 at the bending position (B1; B2), so that when the ultrasonic probe 3 is longitudinally vibrated, the second lateral vibration, which has the same wavelength and vibration direction as the first lateral vibration and which is in anti-phase with respect to the first lateral vibration, has only to be superposed on the longitudinal vibration and the first lateral vibration in the ultrasonic probe 3. Therefore, the first lateral vibration and the second lateral vibration interfere with each other, so that the influence of the first lateral vibration and the second lateral vibration on the longitudinal vibration of the ultrasonic probe 3 is inhibited.

Although the distal asymmetric portion 22 includes the curved part 27 in the first embodiment, this is not a restriction. For example, as in a second modification shown in FIG. 12, the distal asymmetric portion 22 may include a hook-shaped portion 32 instead of the curved part 27. In the present modification, for example, the ultrasonic probe performs the longitudinal vibration while the distal asymmetric portion 22 is hooked to a treatment target such as a living tissue, so that a resection of the hooked treatment target is performed.

Figure 12:
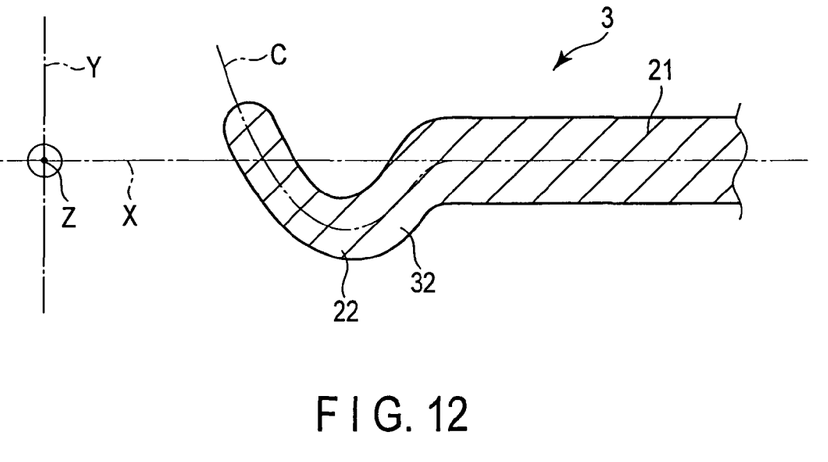
FIG. 12 is a sectional view schematically showing the configuration of a distal asymmetric portion of an ultrasonic probe according to a second modification.

Since the hook-shaped portion 32 is provided, the distal asymmetric portion 22 is shaped asymmetrically with the X-Z plane being the center. Because of the asymmetric shape of the distal asymmetric portion 22, the first lateral vibration is superposed on the longitudinal vibration in the ultrasonic probe 3 while the ultrasonic probe 3 is performing the longitudinal vibration. The vibration direction (vibration directions) of the first lateral vibration is parallel to the X-Y plane and perpendicular to the central axis C. In the present modification, when the ultrasonic probe 3 is longitudinally vibrated, the second lateral vibration, which has the same wavelength and vibration direction as the first lateral vibration and which is in anti-phase with respect to the first lateral vibration, is superposed on the longitudinal vibration and the first lateral vibration in the ultrasonic probe 3, as has been described above in the first embodiment.

Figure 13:
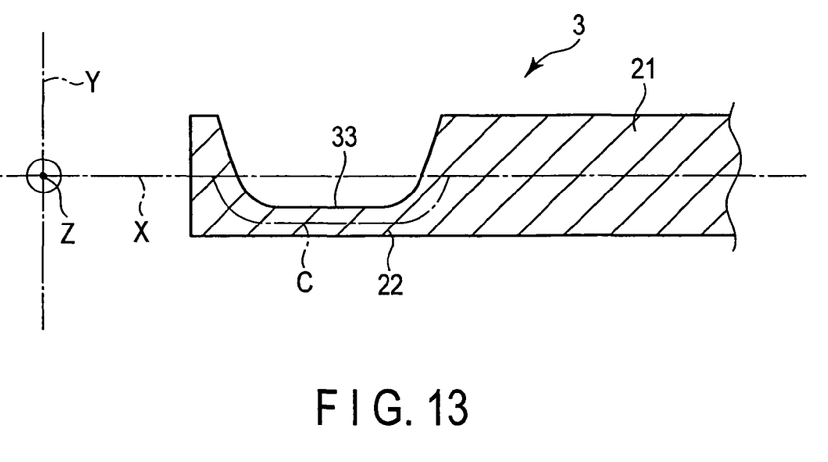
FIG. 13 is a sectional view schematically showing the configuration of a distal asymmetric portion of an ultrasonic probe according to a third modification.

Moreover, for example, as in a third modification shown in FIG. 13, the distal asymmetric portion 22 may include a cutout portion 33 instead of the curved part 27. In the present modification, for example, the ultrasonic probe performs the longitudinal vibration while the distal asymmetric portion 22 is hooked to a treatment target such as a living tissue, so that the hooked treatment target is resected.

Since the cutout portion 33 is provided, the distal asymmetric portion 22 is shaped asymmetrically with respect to the X-Z plane. Because of the asymmetric shape of the distal asymmetric portion 22, the first lateral vibration is superposed on the longitudinal vibration in the ultrasonic probe 3 while the ultrasonic probe 3 is performing the longitudinal vibration. The vibration direction of the first lateral vibration is parallel to the X-Y plane and perpendicular to the central axis C. In the present modification, when the ultrasonic probe 3 is longitudinally vibrated, the second lateral vibration, which has the same wavelength and vibration direction as the first lateral vibration and which is in anti-phase with respect to the first lateral vibration, is superposed on the longitudinal vibration and the first lateral vibration in the ultrasonic probe 3, as has been described above in the first embodiment.

According to the second modification and the third modification described above, the distal asymmetric portion 22 has only to be shaped asymmetrically with the X-Z plane being the center. Because of the asymmetric shape of the distal asymmetric portion 22, the first lateral vibration having a vibration direction which is parallel to the X-Y plane and perpendicular to the central axis C has only to be superposed on the longitudinal vibration in the ultrasonic probe 3 by the longitudinal vibration of the ultrasonic probe 3.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic probe that extends from a proximal end to a distal end along a central axis, the ultrasonic probe being configured to connect to an ultrasonic vibrator and transmit an ultrasonic vibration generated in the ultrasonic vibrator from the proximal end to the distal end so that the ultrasonic probe performs a longitudinal vibration in a vibrating direction, the vibrating direction being parallel to the central axis, the ultrasonic probe comprising:
 a probe body that extends along an X-axis,
  the X-axis being coaxial with the central axis, and
  the probe body being symmetric about the X-axis;
 a distal asymmetric portion that is distal of the probe body,
  the distal asymmetric portion being asymmetric about the X-axis so that (i) a center of gravity of the distal asymmetric portion is deviated from the X-axis and (ii) a first lateral vibration of the distal asymmetric portion is superposed on the longitudinal vibration of the ultrasonic probe,
  a vibrating direction of the first lateral vibration being perpendicular to the central axis of the ultrasonic probe and perpendicular to a Z-axis direction, and
  the Z-axis direction being perpendicular to the X-axis direction; and
 a proximal side probe component that is proximal of the probe body,
  the proximal side probe component being bent relative to the probe body at a bending position so that (i) a center of gravity of the proximal side component is deviated from the X-axis and (ii) a second lateral vibration of the proximal side component is superposed on the longitudinal vibration of the ultrasonic probe,
  an extending direction of the proximal side component being perpendicular to the Z-axis direction and tilted relative to the X-axis,
  a wavelength and a vibrating direction of the second lateral vibration being the same as a wavelength and a vibrating direction of the first lateral vibration, and
  the second lateral vibration being in anti-phase with respect to the first lateral vibration.

2. The ultrasonic probe according to claim 1, wherein:
 the proximal side probe component extends from the proximal end of the ultrasonic probe along the central axis, and
 a first dimension of the probe body along the central axis is larger than a second dimension of the proximal side probe component along the central axis.

3. The ultrasonic probe according to claim 1, wherein an amplitude of the first lateral vibration is the same as an amplitude of the second lateral vibration.

4. The ultrasonic probe according to claim 1, wherein:
 the center of gravity of the distal asymmetric portion is deviated from the X-axis in a first Y-axis direction, the first Y-axis direction being perpendicular to the X-axis, and
 the center of gravity of the proximal side probe component is deviated from the X-axis in a second Y-axis direction, the second Y-axis direction being perpendicular to the X-axis and opposite to the first Y-axis direction.

* * * * *